(12) United States Patent
Moskal et al.

(10) Patent No.: US 11,137,505 B2
(45) Date of Patent: Oct. 5, 2021

(54) METHOD FOR MEDICAL IMAGING IN TOF-PET TOMOGRAPHY

(71) Applicants: UNIWERSYTET JAGIELLONSKI, Cracow (PL); UNIWERSYTET MARII CURIE-SKLODOWSKIEJ, Lublin (PL)

(72) Inventors: Pawel Moskal, Czulowek (PL); Bozena Jasinska, Lublin (PL)

(73) Assignees: UNIWERSYTET JAGIELLONSKI, Cracow (PL); UNIWERSYTET MARII CURIE-SKLODOWSKIEJ, Lublin (PL)

( * ) Notice: Subject to any disclaimer, the term of this patent is extended or adjusted under 35 U.S.C. 154(b) by 387 days.

(21) Appl. No.: 16/332,368

(22) PCT Filed: Sep. 14, 2017

(86) PCT No.: PCT/IB2017/055560
§ 371 (c)(1),
(2) Date: Mar. 12, 2019

(87) PCT Pub. No.: WO2018/051264
PCT Pub. Date: Mar. 22, 2018

(65) Prior Publication Data
US 2020/0081144 A1    Mar. 12, 2020

(30) Foreign Application Priority Data
Sep. 14, 2016 (PL) .......................... 418689

(51) Int. Cl.
*G01T 1/29* (2006.01)
*A61B 6/03* (2006.01)
(Continued)

(52) U.S. Cl.
CPC ............ *G01T 1/2985* (2013.01); *A61B 6/037* (2013.01); *A61B 6/481* (2013.01); *A61B 6/5205* (2013.01);
(Continued)

(58) Field of Classification Search
CPC ..... G01T 1/2985; G01T 1/1647; A61B 6/037; A61B 6/4241; A61B 6/4266; A61B 6/481; A61B 6/5205
See application file for complete search history.

(56) References Cited

U.S. PATENT DOCUMENTS

2016/0216385 A1* 7/2016 Moskal ................. G01T 1/2985

FOREIGN PATENT DOCUMENTS

| WO | 2012135725 | 10/2012 | | |
|---|---|---|---|---|
| WO | WO-2014209972 A1 * | 12/2014 | ........... | A61B 6/5258 |

(Continued)

OTHER PUBLICATIONS

Krzysztof Kacperski et al. "Performance of Three-Photon PET Imaging: Monte Carlo Simulations" arxiv.org. Cornell University Library, 201 Olin Library Cornell University Itaca, NY, 14853, Jul. 12, 2005, XP080202627, DOI: 10.1088/0031-9155/50/019.
(Continued)

*Primary Examiner* — Boniface N Nganga
(74) *Attorney, Agent, or Firm* — Mark M. Friedman

(57) ABSTRACT

The invention relates to a method for reconstruction of an image of a morphometric parameter being a ratio of the frequency of annihilation of an electron with a positron to three and two quanta. The device for imaging the interior of the studied object comprises a series of TOF-PET detection modules (110), a data acquisition subsystem (111), a data selection subsystem (113) configured so as to record and identify all types of quanta emitted from the studied object after administration of an isotopic marker, the data process-
(Continued)

ing system being characterised in that it allows for reconstructing (121, 123, 131, 133, 141) and visualising (143) of a $\delta_{3\gamma}(x,y,z)$ image of the ration of two-quantum and three-quantum annihilations without the necessity to measure the deexcitation quanta.

5 Claims, 1 Drawing Sheet

(51) Int. Cl.
*A61B 6/00* (2006.01)
*G01T 1/164* (2006.01)
(52) U.S. Cl.
CPC ........... *A61B 6/4241* (2013.01); *A61B 6/4266* (2013.01); *G01T 1/1647* (2013.01)

(56) References Cited

FOREIGN PATENT DOCUMENTS

| | | | |
|---|---|---|---|
| WO | WO-2015006123 A1 * | 1/2015 | ........... A61B 6/5205 |
| WO | 2015028604 | 3/2015 | |
| WO | 2017043985 | 3/2017 | |

OTHER PUBLICATIONS

Alkhorayef M et al. "Measurment of Three Gamma Annihilation by Lanthanum-Based Crystals Compared With Nai(TL) and HPGE" Journal of Radianalytical and Nuclear Chemistry, Klauwer Academic Publishers DO, vol. 291, No. 2, Jul. 10, 2011. XP019998192 pp. 493-496.

Kaminska D et al "A Feasibility Study of Ortho-Positronium Decays Measurment With the J-PET Scanner Based on Plastic Scintillators" The European Physical Journal C, Springer Berlin Heidelberg vol. 76, No. 8, Aug. 9, 2019 pp. 1-14 XP036058147.

R. Pietrzak et al. "influence of neoplastic therapy on the investigated blood using positron annihilation lifetime spectroscopy", Nukleonika 2013, 58(1) pp. 199-202.

J. N. Sherwood, "The temperature dependence of positron lifetimes in solid pivalic acid" Chem. Phys., 63, (1981) 51.

B. Jasinska, A.e. Koziol and T. Goworek "Void Shapes and o-Ps lifetime in molecular crystals", Acta Phys. Polon. A95 (1999) 557.

* cited by examiner

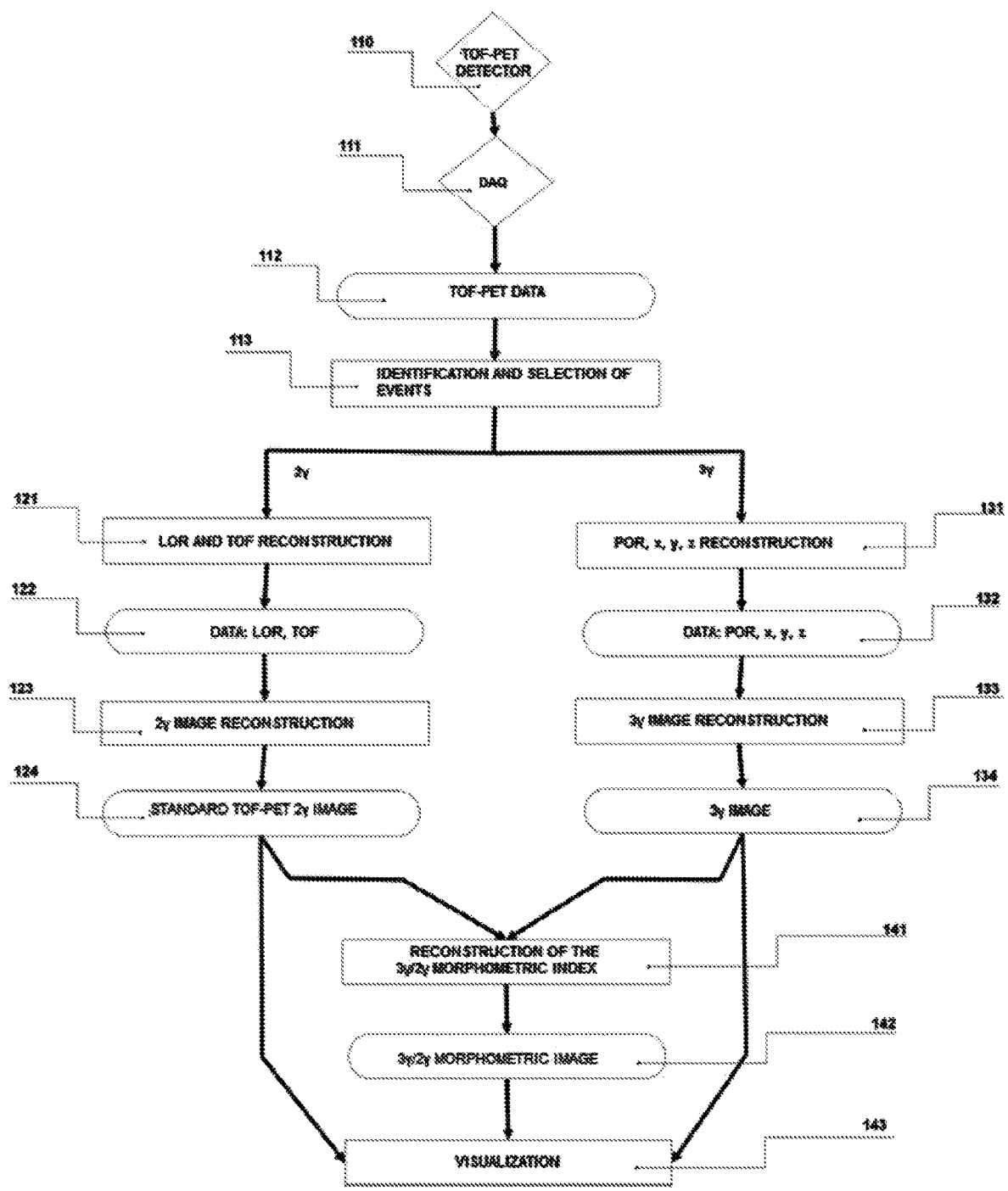

METHOD FOR MEDICAL IMAGING IN TOF-PET TOMOGRAPHY

The invention relates to a method for medical imaging in TOF-PET tomography, based on the ratio of 3γ/2γ quanta which are formed during the electron-positron annihilation. The method described in the present invention may be applied in PET medical diagnosis using pharmaceuticals labelled with any positron-emitting radioisotope.

Positron Emission Tomography (PET) is a commonly known diagnostic method which allows for imaging of metabolism of selected substances in a living organism. Its possible applications include imaging of a patient's body enabling determination of the size and localisation of a neoplasm as well as search for metastases. The PET technique allows for detecting the metastases even at a stage which cannot be detected by other methods, normally used for detection of anatomical or morphological changes.

Prior to PET examination, a patient receives a radiopharmaceutical containing a radioisotope, e.g. $^{18}$F or $^{11}$C, having nuclei which undergo a beta plus decay, emitting a positron. The PET technique used currently is based on annihilation of a positron emitted by a radiopharmaceutical and an electron originating from the patient's body, yielding two quanta, which have an energy of 511 keV each. PET tomographs enable recording of the annihilation quanta (511 keV). For every recorded event, spots of interaction of the quanta in the tomograph and time differences between the interaction events of the recorded quanta (called time of flight, TOF) are determined. Then, knowing the spots and times for a large number of recorded events, a distribution of density of the annihilation spots is reconstructed, corresponding to the image of intensities of the radiopharmaceutical's metabolisation in the patient's organism.

As is described in the Patent Application No. PCT/PL2015/050038, radiopharmaceuticals may be divided in general into two classes depending on the type of radioisotopes used. The first, most frequently used class, comprises isotopes, which after the emission of a positron transform into a daughter nucleus in the ground state. This group includes e.g. $^{18}$F, which as a result of a nuclear reaction emits a positron and is transformed into a stable nucleus of $^{18}$O. The second class of isotopes, including e.g. $^{44}$Sc or $^{14}$O, during a beta plus decay are transformed into a daughter nucleus in the excited state, which emits subsequently the excitation energy in the form of a gamma quantum. Deexcitation of the daughter nucleus occurs almost immediately with an average interval of the order of several picoseconds (e.g. 2.6 ps for $^{44}$Sc).

Although the deexcitation quantum is not used in PET imaging currently, and in fact its interaction in the tomograph may lead to an additional background, Patent Applications Nos. PCT/PL2015/050038 and WO2012/135725 have described recently a possibility to utilise it for simultaneous imaging with several radiopharmaceuticals, and Patent Application No. WO2015/028604 discloses a method for morphometric imaging, utilising a deexcitation quantum for determination of lifetimes of ortho-positronium (o-Ps) atoms formed inside body cells during PET imaging. Application No. WO2015/028604, and then also Application No. PCT/PL2015/050038 describes that in order to define the image of ortho-positronium lifetimes, a deexcitation quantum should be recorded in every event, determining the time of creation of an o-Ps atom, as well as quanta from two- or three-quantum annihilation should be recorded, which allow for defining the moment of decay of the positronium atom. The average ortho-positronium lifetime ($T_{o\text{-}Ps}$) and the probability of its formation ($P_{o\text{-}Ps}$) determined in every voxel of the image serve as a morphological indicator, additional and independent of the Standardised Uptake Value (SUV). In the paper by R. Pietrzak et al. "Influence of neoplastic therapy on the investigated blood using positron annihilation lifetime spectroscopy", NUKLEONIKA 2013, 58 (1): pp. 199-202, it was proved that the lifetimes of orto-positronium atoms in the blood of patients suffering from leukaemia change after radiotherapy.

However, the solution pertaining to morphometric imaging described in the Patent Application No. WO2015/028604 is limited to radiopharmaceuticals containing isotopes which emit a deexcitation quantum, and excludes use of isotopes most common in the PET, such as e.g. $^{18}$F and $^{11}$C, which, while decaying to the ground state of the final nucleus, emit only a positron, not emitting any deexcitation quantum. Moreover, there are no known methods in prior art at present, which could utilise all types of radio-markers used in the PET diagnostics for morphometric imaging.

Therefore, it would be highly desirable to develop a method for measuring a parameter which would replace the direct ortho-positronium lifetime measurements in living organisms, and to apply this method in a tomograph which allows for reconstructing images of this parameter, enabling use of radiopharmaceuticals that contain both isotopes emitting deexcitation quanta, and those which do not emit these quanta.

The solution described in the Patent Application No. WO2015/028604 was based on the observation that there is a correlation between the o-Ps lifetime ($T_{o\text{-}Ps}$) and the size of the void in which the positronium atom is trapped (Eldrup, D. Lightbody, J. N. Sherwood, "The temperature dependence of positron lifetimes in solid pivalic acid", Chem. Phys., 63, (1981) 51). If the sizes of the voids are of the order of angstroms, $T_{o\text{-}Ps}$ is very sensitive to even relatively small changes in the size or shape (B. Jasińska, A. E. Kozioł and T. Goworek "Void shapes and o-Ps lifetime in molecular crystals", *Acta Phys. Polon. A*95 (1999) 557).

The solution according to the present invention is based on other observations, namely:
(i) the size of the void space between molecules is determined by the $f_{oP\text{-}s\text{-}3\gamma}$ fraction of the o-Ps atoms annihilating with 3γ emission. It is a consequence of the correlation between $f_{oPs\text{-}3\gamma}$ and $T_{o\text{-}Ps}$, which may be expressed using the following equation:

$$f_{o\text{-}Ps\text{-}3\gamma} = T_{o\text{-}Ps}/T_{o\text{-}Ps\text{-}vacuum} \quad (1)$$

where $T_{o\text{-}Ps\text{-}vacuum}$ is the value of the o-Ps lifetime in vacuum, equal to 142 ns;
(ii) a change in the $f_{o\text{-}Ps\text{-}3\gamma}$ fraction accompanying a change in the size of the void volume between molecules manifests itself as a change in the $f_{3\gamma2\gamma} = N_{3\gamma}/N_{2\gamma}$ ratio in the positron-electron annihilation into 3γ and into 2γ.

To determine the dependence of $f_{oPs\text{-}3\gamma}$ on the $f_{3\gamma2\gamma}$ ratio measured experimentally by the method according to the present invention, it is necessary to discuss both processes leading to two-quantum annihilation, and three-quantum annihilation.

A positron penetrating a human body (originated for the β$^+$ decay of a radioisotope) may annihilate directly with one of electrons of the studied object or it may form a bound state with an electron—a positronium (Ps) atom. Then, positronium may be trapped inside a void volume between molecules of the studied body. Ps may be formed in two states: para-Ps (in which the positron and the electron have a total spin equal to zero) or ortho-Ps (spins of both particles add up to a spin value equal to 1). According to the laws of conservation of quantum numbers, para-Ps decays with emission of an even number of quanta, mainly 2γ, both in vacuum and in a medium. On the other hand, an o-Ps atom in vacuum annihilates mainly with 3γ emission, while in matter, o-Ps may annihilate additionally into two quanta in a so-called pick-off process—with one of electrons of the surrounding medium. Thus, in the studied medium, o-Ps may annihilate by one of the two processes: some fractions by a spontaneous decay to 3γ, and the remaining fraction—by a pick-off process to 2γ. The ratio of these two fractions depends on the size of the void space. The larger the void space, the longer the o-Ps lifetime is, and the larger the $f_{oPs-3\gamma}$ fraction of annihilation with emission of 3γ quanta.

Free annihilation and the pick-off process occur mainly with 2γ emission, only the 1/372 fraction of these annihilations of a positron with an electron occurs with 3γ emission.

Including both described above pathways for 3γ quanta generation in annihilation processes, the $f_{3\gamma 2\gamma}$ ratio may be expressed as:

$$f_{3\gamma 2\gamma} = \frac{f_{3\gamma}}{1 - f_{3\gamma}} \quad (2)$$

where $f_{3\gamma}$ is the fraction of annihilation to 3γ, having the following form:

$$f_{3\gamma} = \frac{\left(1 - \frac{4}{3}P_{o\text{-}Ps}\right)}{372} + \frac{\tau_{o\text{-}Ps}}{\tau_{o\text{-}Ps\text{-}vacuum}} P_{o\text{-}Ps} \quad (3)$$

where $P_{o\text{-}Ps}$ is the probability of ortho-positronium, depending on properties of the molecular structure of the studied object. While deriving the above dependence, annihilations to four or more gamma quanta were omitted, as their share is of the order of $10^{-6}$ at most; the fact that the pick-off process may occur also by an annihilation to 3γ ($1/372 \times P_{o\text{-}Ps} \times (1-f_{oP\text{-}s\text{-}3\gamma})$) was omitted too, as the share from these processes is insignificant, and moreover, the main goal of deriving the above formula consists in proving that the $f_{3\gamma 2\gamma} = N_{3\gamma}/N_{2\gamma}$ fraction (being a function of the lifetime ($T_{oP\text{-}s}$) and o-Ps formation probability ($P_{o\text{-}Ps}$)) is correlated with sizes and concentration of the voids volumes, thus it may be used as a measure (a morphometric indicator) of porosity of the studied organism's tissues.

The $f_{3\gamma 2\gamma} = N_{3\gamma}/N_{2\gamma}$ fraction may be determined experimentally as a ratio of numbers of events recorded during the object imaging with 3γ and 2γ emissions or from energy spectra, by one of the two methods: "peak to peak" or "peak to valley". However, the latter method is burdened with numerous additional requirements discussed e.g. in the paper "Three-Quantum Annihilation in Porous Vycor Glass" by B. Jasińska, J. Wawryszczuk and R. Zaleski, Acta Phys. Polon. A 107 (2005) 821.

In the human body, positronium atoms may be formed and trapped both in high-density tissues and in biofluids. In tissues, the voids volumes between molecules have sizes of the order of 1 nm so the expected fraction of o-Ps atoms annihilating with 3γ emission is of the order of 1%. To emphasize morphometric differences between the tissues, a morphometric indicator is defined in the present invention, having a form of a relative difference of the $f_{3\gamma 2\gamma}$ ratio in the studied medium $(f_{3\gamma 2\gamma})_t$ and the $(f_{3\gamma 2\gamma})_r$ value in a reference material, expressed as per mille:

$$\delta_{3\gamma} = \frac{(f_{3\gamma 2\gamma})_t - (f_{3\gamma 2\gamma})_r}{(f_{3\gamma 2\gamma})_r} \times 1000\% \quad (4)$$

In living organisms, water constitutes a good reference material. The values of the lifetime and the o-Ps formation probability measured in purified water amount to: $T_{o\text{-}Ps}=1.8$ ns, $P_{o\text{-}Ps}=30\%$ ("Incorporation of the Magnetic Quenching Effect into the Blob Model of Ps Formation. Finite Sized Ps in a Potential Well", Stepanov et al., Mater. Sci. Forum, Vol. 666, 109-114 (2010)). In aqueous solutions, the lifetime increases to approx. $T_{o\text{-}Ps}=2.0$ ns. Based on the published results of investigations pertaining to organic materials (molecular crystals, polymers, long-chain alkanes) and small known number of papers on studies of neoplasms, the expected values of lifetimes ranges from about 1 to about 5 ns, and the o-Ps formation probabilities in a human organism—from about 10 to about 40%. For exemplary values ($T_{oP\text{-}s}=4$ ns and $P_{o\text{-}Ps}=40\%$), the morphometric indicator reaches $\delta_{3\gamma}=50\%_o$, and for the lowest discussed values ($T_{o\text{-}Ps}=1$ ns and $P_{o\text{-}Ps}=10\%$) $\delta_{3\gamma}=-50\%_o$.

The present invention relates to a method for medical imaging in TOF-PET tomography, characterised in that it comprises the following steps:
introduction of an object containing positron-emitting radioisotope into the diagnostic chamber of the tomograph,
recording of gamma quanta emitted from the studied object,
attribution of the recorded events to 2γ and 3γ annihilation subgroups,
reconstruction and normalisation of the 2γ image,
reconstruction and normalisation of the 3γ image,
calculation of the 3γ/2γ ratio for every voxel,
determination of values of the morphometric indicator $\delta_{3\gamma}$ for every voxel,
visualisation of the morphometric image $\delta_\gamma$.

In a preferred embodiment of the invention, the morphometric image $\delta_{3\gamma}$ is determined based on the following dependence:

$$\delta_{3\gamma} = \frac{(f_{3\gamma 2\gamma})_t - (f_{3\gamma 2\gamma})_r}{(f_{3\gamma 2\gamma})_r} \times 1000\%$$

where:
$(f_{3\gamma 2\gamma})_t$ is a ratio of count number of annihilation with 3γ emission to that of annihilation with 2γ emission in the studied material, and $(f_{3\gamma 2\gamma})_r$ is the same ratio in a reference material.

In another preferred embodiment of the invention, two gamma quanta originating from the two-quantum positron-electron annihilation and one or no quantum from the deexcitation are recorded in the defined time interval.

In a further preferred embodiment of the invention, three gamma quanta originating from the three-quantum positron-electron annihilation and one or no quantum from the deexcitation are recorded in the defined time interval.

Preferably, anatomical and/or morphological images of the studied object are created simultaneously or sequentially, and the obtained morphometric image $\delta_{3\gamma}$, is overlaid onto the mentioned anatomical and/or morphological images of the studied object.

Equally preferably, when the studied object contains more than one positron-emitting radioisotope, gamma quanta for every radioisotope are recorded respectively.

BRIEF DESCRIPTION OF FIGURES

The invention is show by means of example embodiment in a drawing, wherein FIG. 1 shows a flow chart of a process for reconstruction of the 3γ/2γ fractions of annihilating positrons in an exemplary TOF-PET detector.

EXAMPLE

For recording of gamma quanta, PET tomographs known in prior art may be used, consisting of both organic and inorganic scintillators, after using the method described in the present invention, which allows for recording both two-quantum and three-quantum annihilations.

In FIG. 1, a flow chart of a procedure for obtaining a 3D image of the 3γ/2γ ratio originating from positron-electron annihilation vs. the location of the studied object is illustrated. Tomograph 110 comprises detectors which allow for determining the position and time of the reaction in the tomograph of gamma quanta emitted from the studied object. Electric signals from the detectors 110 are read and processed into digital form by a data acquisition system (DAQ) 111, and then they are transmitted in step 112 to a recording device, which processes them in step 113 or stores on a disc. Data acquisition may be performed using method known in prior art. A processor 113 identifies detectors which have recorded the quanta from 3γ and 2γ annihilations, using conventional methods known to persons skilled in the art.

The event is identified as recording of two or more quanta in the defined time interval (e.g. of several nanoseconds).

The events classified as 2γ annihilation are used for reconstruction of a metabolic image 124 by TOF-PET methods 121, 122, 123 known in prior art.

The events classified as 3γ annihilation are used for reconstruction of (x,y,z) coordinates of the point, in which the annihilation has occurred, and the plane of response (POR) 132. The identification is carried out using a processor 131, by methods known in prior art (e.g. those described in Patent Application No. WO2015/028604). The plane of response is defined as a plane containing point, in which 3γ interacted with the detectors. In the next step 133, based on the data of 132, a 3γ annihilation density image, 133, is reconstructed.

The conventional 2γ image obtained in the TOF-PET 124 and the 3γ image 134 are used by a processor 141 for reconstruction of a 3γ/2γ morphometric image 142. The reconstructed images 124, 134, and 142 are visualised in step 143. The morphometric image is defined by calculating the value of the $\gamma_{3\gamma}$ parameter for every voxel, according to the dependence (4), where the $f_{3\gamma 2\gamma}$ ratio is determined based on the corresponding normalised 2γ and 3γ images. The image is normalised so as to the integral of the values over all voxels of the normalised 2γ image is equal to the total number of 2γ annihilations which have occurred in the imaged part of the studied object. Analogically, the integral of the events in the whole normalised 3γ image is equal to the total number of 3γ annihilations in the imaged part of the studied object.

To enhance the diagnostic options, prior to the morphometric reconstruction 141, the 2γ image 124 and 3γ image 134 may be improved (i.e. corrected for attenuation of gamma quanta in the studied object) using anatomical or morphological images. The latter may be obtained simultaneously or sequentially by the KT or MR tomographic imaging techniques known in prior art. To improve the diagnostic quality, the obtained 3γ/2γ morphometric images may be overlaid onto anatomical or morphological images.

The described method may be used also in imaging using several isotopes. In such a case, the processor 113 identifies also the signals originating from deexcitation quanta (if recorded) emitted by a certain class of isotopic markers discussed earlier. Energy of these quanta has a value characteristic for each isotope. Thus, in the case of multiisotopic imaging, the two-quantum and three-quantum annihilations events may be classified correspondingly for every isotope, enabling simultaneous imaging using radiopharmaceuticals labelled with radioisotopes from various isotope classes discussed in the present description. It is particularly important e.g. of the case of monitoring of production of various β+-radioactive isotopes during hadron therapy.

The presented method of 3γ/2γ imaging and the morphometric indicator $\delta_{3\gamma}$ have the following advantages:

the $\delta_{3\gamma}$ indicator is a measure of porosity of tissues of the studied organism and serves as a measure of advancement of structural changes in cell on the molecular level;

$\delta_{3\gamma}$ is an additional indicator for SUV—standardised indicator of cell metabolism being defined in PET, and it provides additional information useful in diagnosing;

the 3γ/2γ image does not depend on the time of examination, so it does not need to be corrected for the decrease of the radioisotope activity in the studied object in time, which is of high significance in examinations requiring moving the patient along the scanner to record images of various body parts;

also the $\delta_{3\gamma}$ indicator value does not depend on time elapsed from the administration of the radiopharmaceutical to the patient. Thus, the knowledge of the physical or biological half-life of the radiopharmaceutical, or its initial activity is not necessary to determine the $\delta_{3\gamma}$ value;

the morphometric indicator $\delta_{3\gamma}$ and the SUV indicator may be determined simultaneously during the same examination;

the $\delta_{3\gamma}$ morphometric image may be determined using all radiopharmaceuticals utilised in the PET techniques, thus, as opposite to other morphometric indicator known in prior art, it is not limited only to the class of radioisotopes emitting a deexcitation quantum;

determining the $\delta_{3\gamma}$ value does not require recording of a deexcitation quantum, which leads to an increase in the imaging efficiency while compared to other currently known indicators for morphometric imaging;

the presented system allows for dividing images originating from various radioisotopes in the case of multiisotopic imaging, provided that these isotopes emit deexcitation quanta with various energies.

The technical solutions presented herein are outlined, described and defined in relation to specific preferred applications. However, the discussed various versions of imaging are only examples and they do not exhaust the full scope of the technical solution presented herein. The scope of protection is not limited to the described examples, but only to the following claims.

The invention claimed is:

1. A method for medical imaging in TOF-PET tomography, comprising the following steps:
   introducing an object containing a positron-emitting radioisotope into a diagnostic chamber of a tomograph,
   recording gamma quanta emitted from the object in an imaged volume,
   attributing recorded events to 2γ and 3γ annihilation subgroups,
   reconstructing a 2γ image of the imaged volume,
   reconstructing a 3γ image of the imaged volume,
   normalising the 2γ image to obtain a normalised 2γ image so that the integral of values over all voxels of the normalized 2γ image is equal to the total number of 2γ annihilations which have occurred in the imaged volume,
   normalising the 3γ image to obtain a normalised 3γ image so that the integral of values over all voxels of the normalised 3γ image is equal to the total number of 3γ annihilations which have occurred in the imaged volume,
   determining a value of a morphometric indicator $\delta_{3\gamma}$ for every voxel of the imaged volume based on the following dependence:

$$\delta_{3\gamma} = \frac{(f_{3\gamma 2\gamma})_t - (f_{3\gamma 2\gamma})_r}{(f_{3\gamma 2\gamma})_r} \times 1000\%$$

where:
   $(f_{3\gamma 2\gamma})_t$ is a ratio of count number of annihilations with 3γ emission to a count number of annihilations with 2γ emission, calculated for every voxel of the imaged volume basing on the normalized 2γ image and the normalized 3γ image, and $(f_{3\gamma 2\gamma})_r$ is a ratio of count number of annihilations with 3γ emission to a count number of annihilations with 2γ emission in a reference material,
   visualising the morphometric image of the imaged volume, having voxels of values basing on the determined values of the morphometric indicators $\delta_{3\gamma}$.

2. The method according to claim 1, comprising, in a defined time interval, recording two gamma quanta originating from a two-quantum positron-electron annihilation and recording one gamma quantum or no quantum from a deexcitation.

3. The method according to claim 1, comprising, in a defined time interval, recording three gamma quanta originating from a three-quantum positron-electron annihilation and recording one gamma quantum or no quantum from a deexcitation.

4. The method according to claim 1, comprising creating at least one of: an anatomical image and a morphological image of the object, and overlaying the $\delta_{3\gamma}$ image onto the at least one of the anatomical image and the morphological image of the object.

5. The method according to claim 1, wherein the object comprises more than one positron-emitting radioisotope, and the method comprises recording the gamma quanta for each radioisotope.

* * * * *